(12) United States Patent
Eriksson et al.

(10) Patent No.: US 11,607,559 B2
(45) Date of Patent: Mar. 21, 2023

(54) EVALUATION OF ARCS FOR A RADIATION TREATMENT PLAN

(71) Applicant: RaySearch Laboratories AB, Stockholm (SE)

(72) Inventors: Kjell Eriksson, Bålsta (SE); Albin Fredriksson, Stockholm (SE); Henrik Olsson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 476 days.

(21) Appl. No.: 16/646,267

(22) PCT Filed: Sep. 7, 2018

(86) PCT No.: PCT/EP2018/074210
§ 371 (c)(1),
(2) Date: Mar. 11, 2020

(87) PCT Pub. No.: WO2019/052925
PCT Pub. Date: Mar. 21, 2019

(65) Prior Publication Data
US 2020/0282235 A1    Sep. 10, 2020

(30) Foreign Application Priority Data

Sep. 12, 2017  (EP) .................................. 17190726

(51) Int. Cl.
*A61N 5/10* (2006.01)
(52) U.S. Cl.
CPC .......... *A61N 5/1031* (2013.01); *A61N 5/1045* (2013.01); *A61N 5/1048* (2013.01); *A61N 5/1081* (2013.01); *A61N 2005/1035* (2013.01)

(58) Field of Classification Search
CPC ...... A61N 5/10; A61N 5/1031; A61N 5/1081; A61N 5/1045; A61N 5/103; A61N 5/1048; A61N 5/1047; A61N 2005/1035
See application file for complete search history.

(56) References Cited

U.S. PATENT DOCUMENTS 10,500,417 B2 * 12/2019  Kuusela ............... A61N 5/1045
11,291,858 B2 *  4/2022  MacDonald ........... G16H 20/40
(Continued)

OTHER PUBLICATIONS

Smyth, Gregory et al., "Non-coplanar trajectories to improve organ at risk sparing in volumetric modulated arc therapy for primary brain tumors," Radiotherapy and Oncology 121 (2016) 124-131.

*Primary Examiner* — Jurie Yun
(74) *Attorney, Agent, or Firm* — Faegre Drinker Biddle & Reath LLP

(57) ABSTRACT

It is provided a method for determining arc costs. The method comprises the steps of: determining a plurality of beam orientations; evaluating a set of at least one cost function comprising an intermediate exposure cost function that is evaluated by performing the substeps of: projecting the at least one target volumes on a beam plane; determining an alignment angle based on a collimator angle value; finding any intermediate area in the beam plane along the alignment angle between areas of the at least one target volume projection; determining a value of the intermediate exposure cost function. The method further comprises the steps of: finding a plurality of arcs, wherein each arc comprises a sequence of a plurality of beam orientations; and calculating, for each arc in the plurality of arcs, at least one arc cost based on the cost function values of the beam orientations of the arc.

15 Claims, 7 Drawing Sheets

(56) References Cited

U.S. PATENT DOCUMENTS

| | | | |
|---|---|---|---|
| 11,344,747 B2* | 5/2022 | MacDonald | ......... A61N 5/1045 |
| 2003/0086530 A1 | 5/2003 | Otto | |
| 2008/0298550 A1 | 12/2008 | Otto | |
| 2013/0131428 A1 | 5/2013 | Jiang et al. | |
| 2021/0244970 A1* | 8/2021 | Macdonald | .......... A61N 5/1082 |

* cited by examiner

EVALUATION OF ARCS FOR A RADIATION TREATMENT PLAN

This application is the National Stage of International Application No. PCT/EP2018/074210, filed Sep. 7, 2018, and claims benefit of European Patent Application No. 17190726.4, filed Sep. 12, 2017, the entire contents of which are incorporated by reference herein.

TECHNICAL FIELD

The invention relates to a method, a treatment planning system, a computer program and a computer program product for evaluation of arcs for a radiation treatment plan.

BACKGROUND

In radiation therapy, a target volume is irradiated by one or several therapeutic beams. Various types of therapeutic beams can be used, e.g. photon, electron and ion beams. The target volume can e.g. represent a cancer tumor. The therapeutic beam penetrates the irradiated tissue and delivers an absorbed dose to kill the tumor cells.

One way of providing radiation to the target volume is to use Volumetric Modulated Arc Therapy (VMAT), where the radiation flows during motion, e.g. during motion of the gantry. This allows for shorter treatment times compared to turning radiation off during motion. However, determining suitable arcs of such a treatment plan is a very complex task and is quite different from determining doses to be provided from a set of fixed positions.

Smyth et al "Non-coplanar trajectories to improve organ at risk sparing in volumetric modulated arc therapy for primary brain tumors", Radiotherapy and Oncology 121 (2016) 124-131 discloses an evaluation of non-coplanar volumetric modulated arc radiotherapy (VMAT) trajectories for organ at risk (OAR) sparing in primary brain tumor radiotherapy.

However, if there were to be a way in which arc evaluation is improved further, this would be of great benefit.

SUMMARY

An object of embodiments presented herein is to improve evaluation of arcs for use in radiation therapy.

According to a first aspect of the invention, it is provided a method for determining arc costs of respective potential arcs of a treatment plan for use in radiation therapy targeting at least one target volume. The method is performed in a treatment planning system and comprises the steps of: determining a plurality of beam orientations, wherein each beam orientation comprises respective values of a couch angle, a collimator angle and a gantry angle, each beam orientation defining a beam direction through the collimator; evaluating, for each beam orientation, a set of at least one cost function, wherein the at least one cost function comprises an intermediate exposure cost function that is evaluated by performing the substeps of: projecting the at least one target volumes on a beam plane being a normal plane to the beam direction of the beam orientation; determining an alignment angle based on the collimator angle value; finding any intermediate area in the beam plane along the alignment angle between areas of the at least one target volume projection, such that there is at most one intermediate area crossed by each line parallel to the alignment angle; determining a value of the intermediate exposure cost function based on the any intermediate area. The method further comprises the steps of: finding a plurality of arcs, wherein each arc comprises a sequence of a plurality of beam orientations; and calculating, for each arc in the plurality of arcs, at least one arc cost based on the cost function values of the beam orientations of the arc.

The solution presented herein takes into account that the collimator amounts to a physical limitation of the treatment machine. This enables us to discard beam orientations that would be considered beneficial, e.g. by the method of Smyth et al, but that cannot be realized in a beneficial way by the treatment machine. It also enables us to optimize an additional degree of freedom (the collimator angle) compared to the prior art.

The step of finding any intermediate area may comprise finding any intermediate area between different target volume projections.

The method may further comprise the step of: selecting at least one arc for use in the treatment plan based on the respective arc costs.

The step of finding an intermediate area may comprise finding, for each of a plurality of parallel strips along the alignment angle, a strip area between areas of the at least one target volume projection, wherein each strip is associated with a pair of leafs of a multileaf collimator.

The step of finding an intermediate area may comprise performing a fluence map optimization for the beam orientation and segmenting the optimized fluence map into one or more multileaf collimator settings.

The method may further comprise: projecting at least one organ at risk on the beam plane; and subtracting any overlap area, where an organ at risk projection and a target volume projection overlap, from the overlapped target volume projection.

The method may further comprise the step of: projecting at least one organ at risk on the beam plane; in which case, in the step of evaluating a set of at least one cost function, the set of at least one cost function comprises a function which penalizes any overlap area, where an organ at risk projection and the intermediate area overlap.

In the step of evaluating a set of at least one cost function, the set of at least one cost function may comprise an intermediate dose function which quantifies an estimate of a dose to the at least one target volume.

In the step of evaluating a set of at least one cost function, the set of at least one cost function may comprise at least one constituent function of a treatment plan optimization. This reduces the gap between the heuristic used for determining arc trajectories and the true quality of the determined trajectories.

In the step of evaluating a set of at least one cost functions, the set of at least one cost function may comprise at least one function penalizing the intermediate area size from each beam orientation compared to the minimum intermediate area size over all beam orientations.

The step of calculating at least one arc cost may comprise calculating, for each arc in the plurality arcs, an aggregate arc cost based on the cost function values of the beam orientations of the arc.

The step of calculating at least one arc cost may comprise calculating, for each arc in the plurality of arcs, an aggregate arc cost based on an estimate of a dose to the at least one target volume provided by the combined exposure of the beam orientations of the arc.

According to a second aspect of the invention, it is provided a treatment planning system for determining arc costs of respective potential arcs of a treatment plan for use in radiation therapy targeting at least one target volume. The treatment planning system comprises: a processor; and a memory storing instructions that, when executed by the processor, cause the treatment planning system to: determine a plurality of beam orientations, wherein each beam orientation comprises respective values of a couch angle, a collimator angle and a gantry angle, each beam orientation defining a beam direction through the collimator; evaluate, for each beam orientation, a set of at least one cost function, wherein the at least one cost function comprises an intermediate exposure cost function that is evaluated by executing instructions that cause the treatment planning system to: project the at least one target volumes on a beam plane being a normal plane to the beam direction of the orientation set; determine an alignment angle based on the collimator angle value; find any intermediate area in the beam plane along the alignment angle between areas of the at least one target volume projection, such that there is at most one intermediate area crossed by each line parallel to the alignment angle; determine a value of the intermediate exposure cost function based on the any intermediate area. The memory further comprises instructions that, when executed by the processor, cause the treatment planning system to: find a plurality of arcs, wherein each arc comprises a sequence of a plurality of beam orientations; and calculate, for each arc in the plurality of arcs, at least one arc cost based on the cost function values of the beam orientations of the arc.

According to a third aspect of the invention, it is provided a computer program for determining arc costs of respective potential arcs of a treatment plan for use in radiation therapy targeting at least one target volume. The computer program comprises computer program code which, when run on a treatment planning system causes the treatment planning system to: determine a plurality of beam orientations, wherein each beam orientation comprises respective values of a couch angle, a collimator angle and a gantry angle, each beam orientation defining a beam direction through the collimator; evaluate, for each beam orientation, a set of at least one cost function, wherein the at least one cost function comprises an intermediate exposure cost function that is evaluated by running computer program code which, when run on the treatment planning system causes the treatment planning system to: project the at least one target volumes on a beam plane being a normal plane to the beam direction of the orientation set; determine an alignment angle based on the collimator angle value; find any intermediate area in the beam plane along the alignment angle between areas of the at least one target volume projection, such that there is at most one intermediate area crossed by each line parallel to the alignment angle; determine a value of the intermediate exposure cost function based on the any intermediate area. The computer program further comprises computer program code which, when run on a treatment planning system causes the treatment planning system to: find a plurality of arcs, wherein each arc comprises a sequence of a plurality of beam orientations; and calculate, for each arc in the plurality of arcs, at least one arc cost based on the cost function values of the beam orientations of the arc.

According to a fourth aspect of the invention, it is provided a computer program product comprising a computer program according to claim the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

According to embodiments presented herein, a possible beam space is discretized in a finite number of beam orientations, where each beam orientation comprises values of couch angle, collimator angle and gantry angle. Each beam orientation is then evaluated using one or more cost function. This includes evaluation of intermediate space between sections of target volume projections, where a multileaf collimator is unable to block the intermediate space while allowing radiation of the target volume projections. Due to the one-dimensional configurability of the multileaf collimator, the collimator angle is a large factor when evaluating the intermediate area. By considering this intermediate area when evaluating different beam orientations, favorable collimator angles are preferred, thus leading to better arc determinations.

Figure 1:
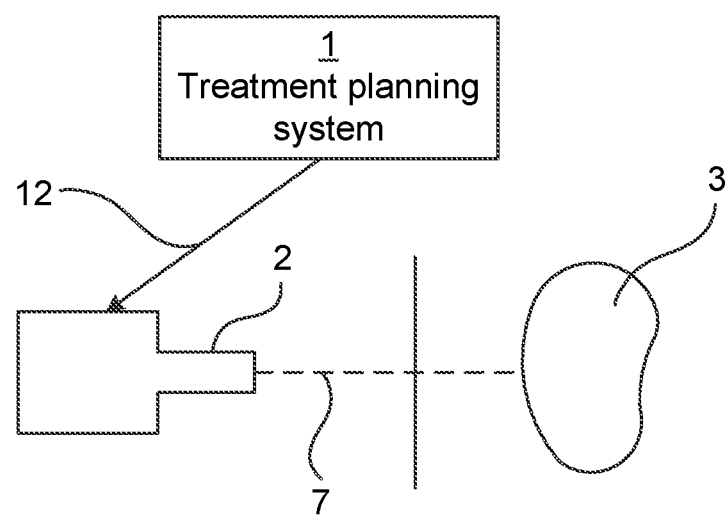
FIG. 1 is a schematic drawing illustrating an environment in which embodiments presented herein can be applied.

FIG. 1 is a schematic drawing illustrating an environment in which embodiments presented herein can be applied. A treatment planning system 1 determines one or more arc trajectories for use when providing beam therapy. This is communicated as a treatment plan 12 to a treatment machine 2. The treatment plan 12 defines how the treatment machine should provide beams and how geometries of the treatment machine are to be changed. Based on the treatment plan, the treatment machine 2 provides a beam 7 to one or more target volumes 3 of a patient.

The way in which the treatment machine 2 generates the beam and delivers the dose differs depending on the treatment modality (such as photons, electrons, or ions) as is well known in the industry per se. However, the common goal is to deliver a dose to the target volume (i.e. the tumor) that is as close as possible to a prescribed dose while minimizing the dose to organs at risk, which depend on where the tumor is located.

Figure 2:
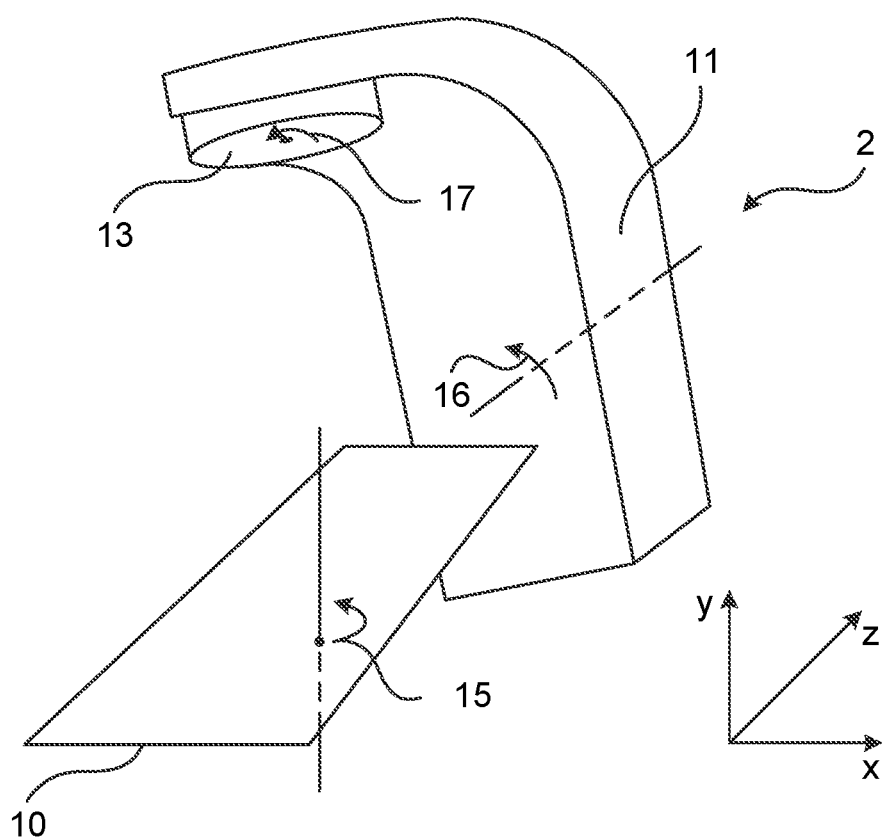
FIG. 2 is a schematic perspective view of a treatment machine, illustrating various angles of a beam orientation set.

FIG. 2 is a schematic perspective view of a treatment machine 2, illustrating various angles of a beam orientation set. A Cartesian coordinate system in dimensions x, y, and z is also shown.

A gantry 11 is rotatable around a gantry axis which is here parallel to the z axis. A gantry angle 16 defines the extent of the gantry rotation. It is not important from where the gantry angle 16 is defined, as long as this definition is consistent.

A couch 10 is provided on which the patient (not shown) lies during treatment. Various fixation mechanisms, known per se, can be applied to ensure the treatment section of the patient is fixated in a known position. The couch 10 is rotatable around a couch axis which is here parallel to the y axis. A couch angle 15 defines the extent of the couch rotation. It is not important from where the couch angle 15 is defined, as long as this definition is consistent.

A multileaf collimator 13 is provided mounted to the gantry 11, through which the radiation is provided during treatment. The multileaf collimator 13 is rotatable around a collimator axis. The collimator axis varies in its orientation (of the Cartesian coordinate system) depending on the rotation of the gantry 11. A collimator angle 17 defines the extent of the rotation of the multileaf collimator. It is not important from where the collimator angle 17 is defined, as long as this definition is consistent.

A combination of values of the couch angle 15, the collimator angle 17 and the gantry angle 16 together forms a beam orientation. The beam orientation defines at what angle radiation will treat the patient. A beam plane is a normal plane to a beam direction, i.e. the collimator axis. In other words, the beam direction is a direction through the collimator, parallel to the collimator axis, towards to couch 10.

Each trajectory occurs in an arc from a start time to an end time and defines motion between beam orientations (optionally via intermediate beam orientations). In other words, the arc trajectory defines a motion implemented using a change in one or more of the couch angle 15, the collimator angle 17 and the gantry angle 16, defined by beam orientations. In one embodiment, radiation is turned on for the whole duration of each arc trajectory. The speed of motion during the arc trajectory can be constant or can vary.

Figure 3:
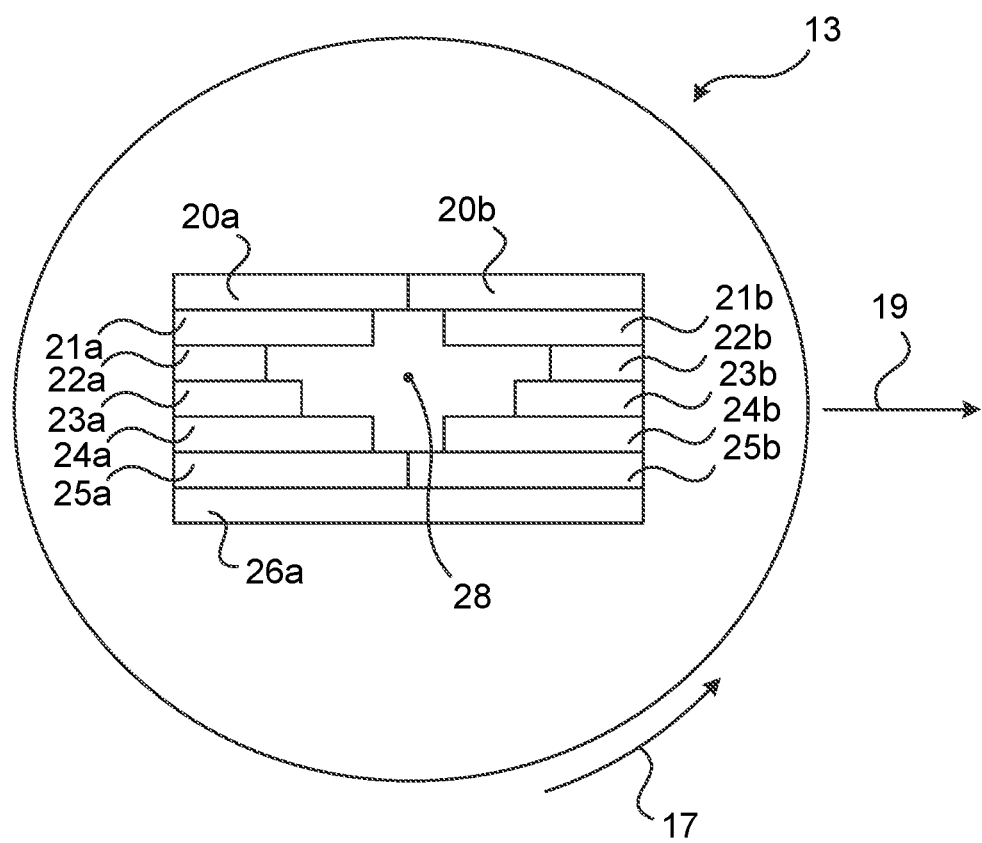
FIG. 3 is a schematic drawing illustrating the multileaf collimator of FIG. 2.

FIG. 3 is a schematic drawing illustrating the multileaf collimator 13 of FIG. 2. The multileaf collimator 13 comprises pairs of leaves 20a-b, 21a-b, . . . , 26a-b. Each leaf is movable in one dimension only, along an alignment angle 19. The alignment angle 19 depends on the collimator angle 17 and can even be equal to the collimator angle. In FIG. 3, the alignment angle 19 is horizontal. Due to the pair-wise configuration of the leaves, each alignment angle 19 is equivalent to its opposite, +−π radians. In other words, the alignment angle 19 defines the direction along which the collimator leaves are movable.

Each pair of opposing leaves can be positioned to provide a space in between the leaves. In this way, an opening 28 can be defined through which radiation can flow. The opening 28 can be tailored to cover a target volume 3, while reducing radiation to surrounding tissue. Since the leaves 20a-b, 21a-b, . . . , 26a-b are only movable along the alignment angle, the possible shapes of the opening 28 depend on the rotation 17 of the multileaf collimator 13. This is illustrated in more detail in FIGS. 4A-4D and is described next.

Figure 4A:
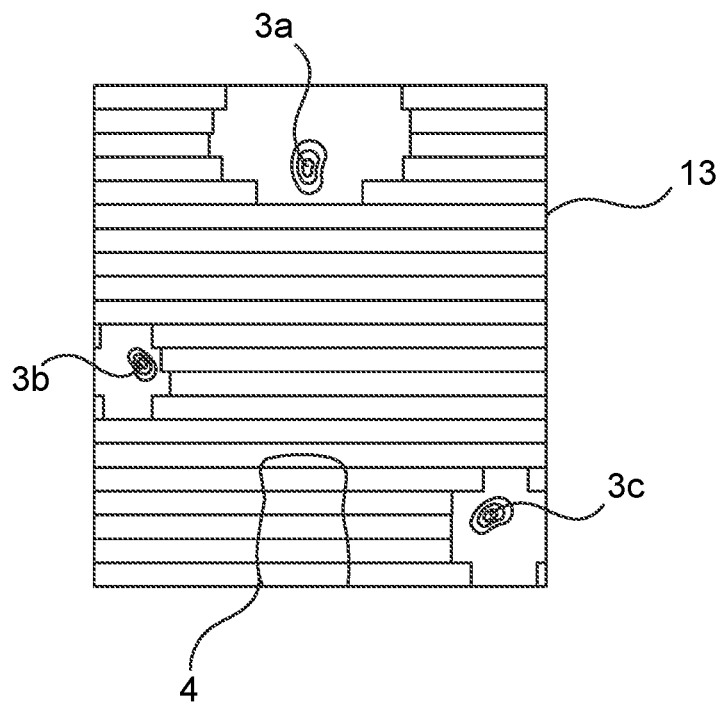
FIGS. 4A-4D are schematic drawings illustrating how different collimator angles affect the intermediate area between target volumes.
Figure 4B:
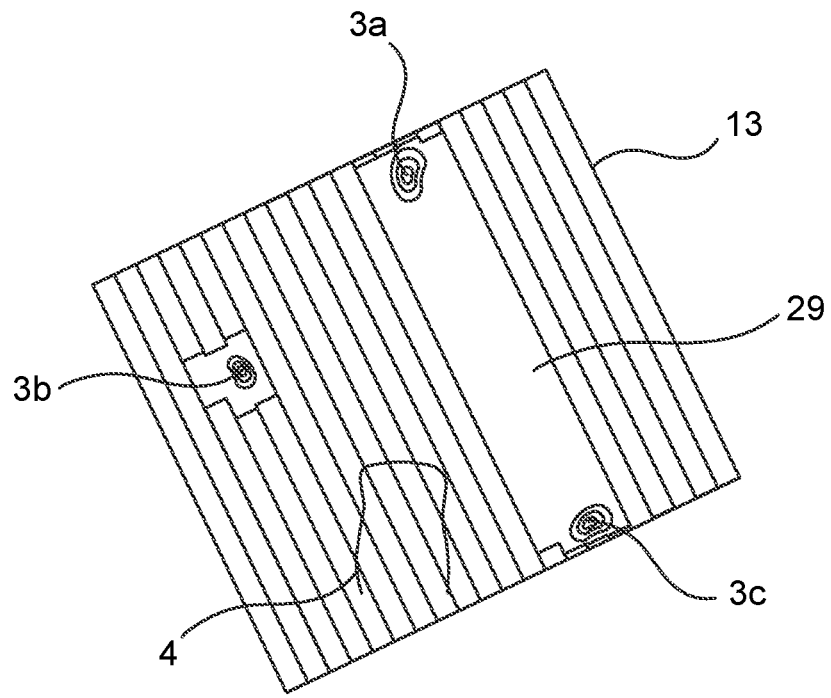

FIGS. 4A-D are schematic drawings illustrating how different collimator angles affect the intermediate area between target volumes. In FIGS. 4A-B, there is here a first target volume 3a, a second target volume 3b and a third target volume 3c. Furthermore, there is an organ at risk 4, for which irradiation should be avoided.

In FIG. 4A, the multileaf collimator can be arranged such that openings are tailored to each target volume 3a, 3b, 3c.

However, in FIG. 4B, when there needs to be an opening for both the first target volume 3a and the third target volume 3c, this needs to be the same opening due to the alignment angle. Hence, a significant intermediate area 29 will form part of the opening, thus causing radiation in the intermediate area 29 if treatment occurs according to this configuration.

The only difference between FIG. 4A and FIG. 4B is the alignment angle, which depends on the collimator angle. It is thus shown how the collimator angle is of utmost importance for reducing radiation for tissue outside the target volumes.

Figure 4C:
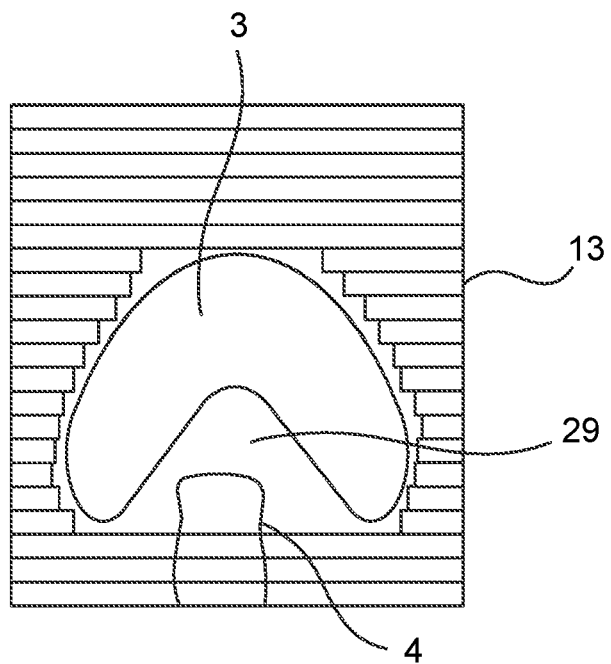
Figure 4D:
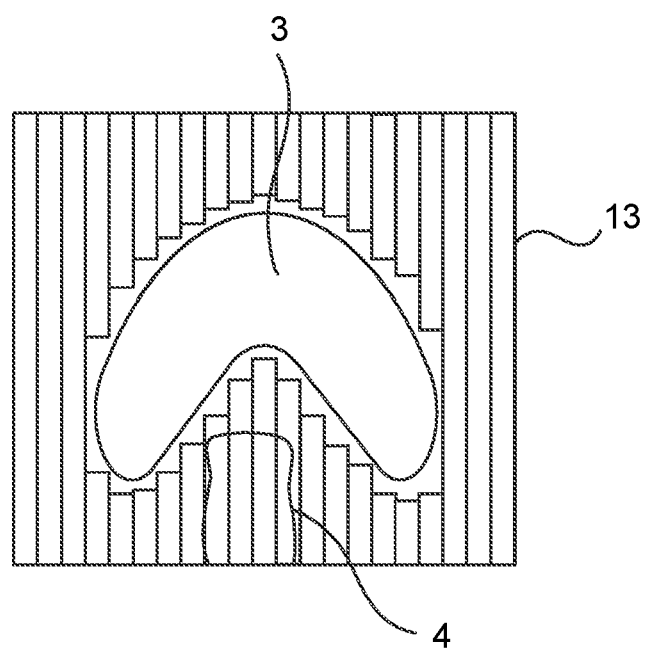

FIGS. 4C-4D show a scenario with a single target volume 3. However, the target volume has protrusions, whereby the collimator angle affects treatment greatly.

In FIG. 4C, the multileaf collimator is unable to be configured to irradiate the lower part of the target volume 3 while preventing irradiation of the organ at risk 4, since there is an intermediate area 29 between the protrusions of the target volume 3.

However, with a π/2 shift in collimator angle, as illustrated in FIG. 4D, there is no intermediate area between the protrusions, and irradiation of the organ at risk 4 can be completely avoided.

Also here, the only difference between FIG. 4C and FIG. 4D is the alignment angle, which depends on the collimator angle. It is thus shown how the collimator angle is of utmost importance for reducing radiation for tissue outside a single target volume with protrusions.

Figure 5:
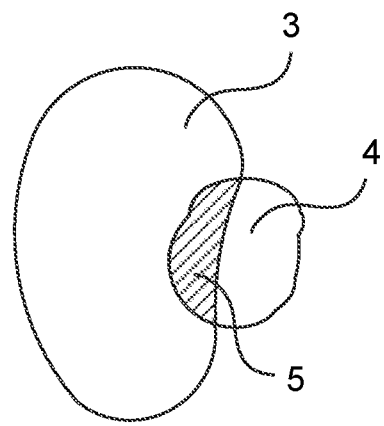
FIG. 5 is a schematic diagram illustrating a situation where a target volume projection overlaps a projection of an organ at risk.

FIG. 5 is a schematic diagram illustrating a situation where a target volume projection overlaps a projection of an organ at risk. The projection is a projection of a three dimensional volume, in this case the target volume, to the beam plane which, being a normal plane to a beam direction of the beam orientation, defined by the beam orientation. In this projection, there is an overlap 5 between the target volume projection 3 and an organ at risk projection 4.

Figure 6:
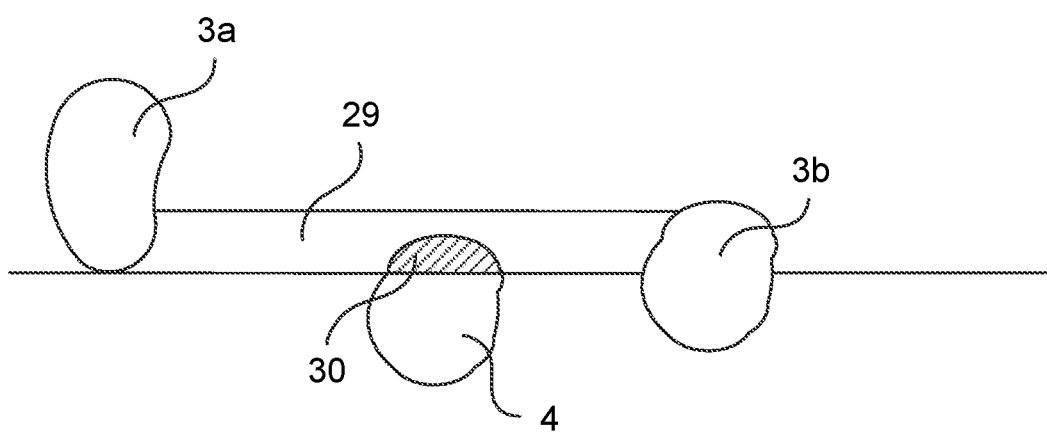
FIG. 6 is a schematic diagram illustrating a situation where a projection of an organ at risk overlaps an intermediate area between target volume projections.

FIG. 6 is a schematic diagram illustrating a situation where a projection of an organ at risk overlaps an intermediate area between target volume projections, here represented by a first target volume projection 3a and a second target volume projection 3b. In this projection, there is an overlap 30 between an intermediate area 29 (between the target volume projections 3a-b) and an organ at risk projection 4. This is of course a situation which should ideally be avoided, since if both target volumes are to be irradiated, this will cause the intermediate area 20 to be irradiated, which includes the organ at risk projection 4 of the overlap 30.

Figure 7A:
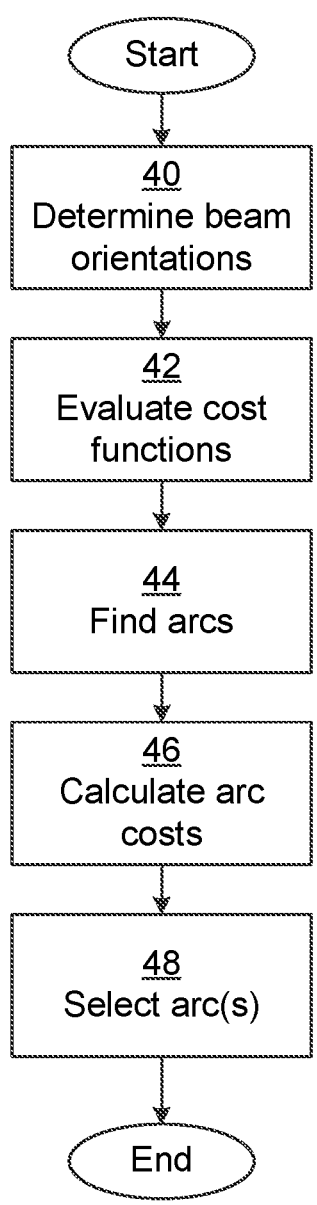
FIGS. 7A-7B are flow charts illustrating embodiments of a method performed in the treatment planning system of FIG. 1 for determining arc costs of respective potential arcs of a treatment plan.
Figure 7B:
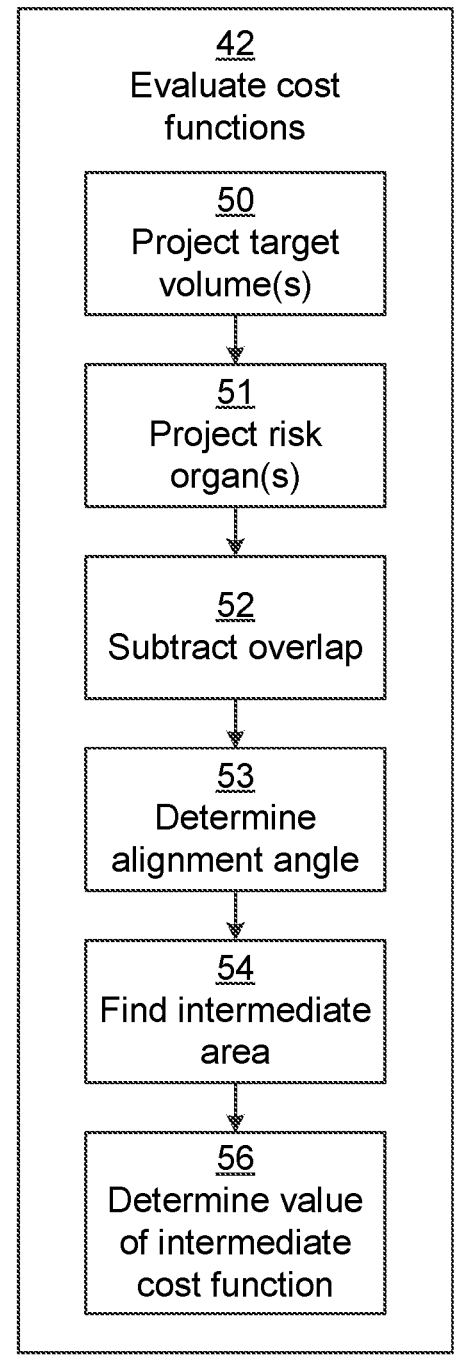

FIGS. 7A-B are flow charts illustrating embodiments of a method performed in the treatment planning system of FIG.

1 for determining arc costs of respective potential arcs of a treatment plan. The arcs can be used in treatment where irradiation occurs during motion, e.g. for VMAT or Dynamic Conformal Arcs (DCA). First, the method illustrated by FIG. 7A will be described. As described above, the treatment plan is for use in radiation therapy targeting at least one target volume.

In a determine beam orientations step 40, the treatment planning system determines a plurality (i.e. a limited set) of beam orientations. Each beam orientation comprises respective values of a couch angle, a collimator angle and a gantry angle. Each beam orientation defines a beam direction through the collimator. By determining a limited set of beam orientations, all possible beam orientations are discretized into a manageable number of beam orientations. It is to be noted that only beam orientations covering 7t radians of collimator angles need to be considered, since the other a radians are equivalent. The plurality of beam orientations could comprise beam orientations where all angles are allowed to vary, or could comprise beam orientations where only one or two of the angles are allowed to vary.

In an evaluate cost functions step 42, the treatment planning system evaluates, for each beam orientation, a set of at least one cost function. In other words, each beam orientation is evaluated to determine its performance, e.g. in terms of irradiating target volume(s) and avoiding irradiating organs at risk or surrounding tissue.

The set of at least one cost function can comprise a function which penalizes any overlap area, where an organ at risk projection and the intermediate area overlap, e.g. the overlap 30 illustrated in FIG. 6.

The set of at least one cost function can comprise an intermediate dose function which quantifies an estimate of a dose to the at least one target volume. This can include penalizing any dose over a predetermined level in an organ at risk. All of this is based on a calculation of dose distribution to the patient from the beam orientation being evaluated.

The set of at least one cost function can comprise at least one constituent function of a treatment plan optimization. For instance, the dose distribution calculation can be used for the constituent function(s). The actual treatment plan optimization, which can e.g. include collimator leaf position, is known in the art per se and occurs after the arcs have been determined.

The set of at least one cost function can comprise at least one function penalizing the intermediate area size from each beam orientation compared to the minimum intermediate area size over all beam orientations. In this way, beam orientations with a small intermediate area size are preferred, thus reducing irradiation of tissue outside the target volume(s).

One or more composite cost function can be calculated by combining the mentioned cost functions.

The cost function evaluation is described in more detail below with reference to FIG. 7B.

In a find arcs step 44, the treatment planning system finds a plurality of arcs, wherein each arc comprises a sequence of a plurality of beam orientations. In one embodiment, the couch and collimator angles are not allowed to vary during the delivery, i.e. all beam orientations of the arc have the same couch angle and/or collimator angle, but different arcs may have different couch angles and/or collimator angles. In this case, it is possible to evaluate all potential arcs by enumeration. In another embodiment, the couch and/or collimator angles are allowed to vary during the delivery. If the arc cost function is linear, it is possible to calculate the cost of all arcs efficiently by dynamic programming (e.g. shortest path algorithms such as Dijkstra's algorithm). Otherwise, it may be computationally demanding to calculate the cost of all arcs. In that case, the costs of the arcs in a subset of the possible arcs could be evaluated, and local search heuristics, such as nearest neighborhood search, or global search heuristics, such as simulated annealing, could be employed starting from the best arcs in the subset.

In a calculate arc costs step 46, the treatment planning system calculates, for each arc in the plurality of arcs, at least one arc cost based on the cost function values of the beam orientations of the arc.

Optionally, this comprises calculating, for each arc in the plurality arcs, an aggregate arc cost based on the cost function values of the beam orientations of the arc. For instance, all corresponding cost function values of the respective beam orientations can be added or averaged to obtain the aggregate arc cost.

Optionally, a map of forbidden angles could be considered to exclude forbidden angles to stay within machine limitations and to avoid patient collision.

The arc costs could be evaluated for arcs of a fixed, pre-determined length, or the length of the arc could be taken into consideration by the value-predicting function.

Optionally, this comprises calculating, for each arc in the plurality of arcs, an aggregate arc cost based on an estimate of a dose provided by the combined exposure of the beam orientations of the arc. In such a case, the complete dose distribution can be considered, i.e. not only dose provided to the at least one target area. In one embodiment, the set of at least one arc cost can comprise at least one constituent function of a treatment plan optimization, which improves correspondence with subsequent optimization.

In an optional select arc(s) step 48, the treatment planning system selects at least one arc for use in the treatment plan based on the respective arc costs. For instance an arc with minimum arc cost can be selected.

Looking now to FIG. 7B, substeps of the evaluate cost functions step 42 are illustrated.

In a project target volume(s) step 50, the treatment planning system projects the at least one target volumes on a beam plane. As explained above, the beam plane is a normal plane to the beam direction of the beam orientation.

In a project risk organ(s) step 51, the treatment planning system projects at least one organ at risk on the beam plane.

In a subtract overlap step 52, the treatment planning system subtracts any overlap area where an organ at risk projection and a target volume projection overlap, from the overlapped target volume projection. In this way, a risk of irradiating the organ at risk is reduced.

In a determine alignment angle step 53, the treatment planning system determines an alignment angle based on the collimator angle value. For instance, the alignment angle can be the collimator angle value.

In a find intermediate area step 54, the treatment planning system finds any intermediate area (see 29 of FIGS. 4A-B and FIG. 5) in the beam plane along the alignment angle between areas of the at least one target volume projection, such that there is at most one intermediate area crossed by each line parallel to the alignment angle. In other words, since there are pairs of leaves of the multileaf collimator, there cannot be more than one intermediate area between a pair of collimator leaves. There can only be zero or one intermediate area between areas of the at least one target volume projection.

As shown in a first example in FIGS. 4A-B and in a second example in FIGS. 4C-D and explained above, the presence or absence of an intermediate area depends on the beam orientation and on the target volume(s). FIGS. 4A-B as well as FIGS. 4C-D illustrate this clearly for different values of alignment angle, i.e. the angle along which the collimator leaves can move.

Hence, each intermediate area comprises non-target area between sections of target area. The sections of target area on either side of the non-target area can either be excluded from the definition of intermediate area or be included in the definition of intermediate area. Optionally, a margin is included in either side of the intermediate area.

Optionally, this comprises finding any intermediate area between different target volume projections, i.e. relating to different target volumes. Alternatively or additionally, this comprises finding any intermediate area between protrusions of each target volume projection, i.e. relating to a single target volume.

Optionally, this comprises finding, for each of a plurality of parallel strips along the alignment angle, a strip area between areas of the at least one target volume projection, wherein each strip is associated with a pair of leafs of a multileaf collimator, e.g. as illustrated in FIG. 3.

Optionally, this comprises performing a fluence map optimization for the beam orientation, in which the fluence for the beam orientation is optimized freely to yield a good dose distribution with respect to the optimization functions of the treatment plan optimization problem. Alternatively, the fluence map could be determined by forward planning. The fluence map could then be converted into intermediate areas by truncation, in which all fluence bixels (each bixel corresponds to a pixel in the beam plane) with values above some cutoff level are truncated to 1 and all fluence bixels with values below the cutoff level are truncated to 0, followed by a modification of the bixel values to make rows of bixels with value 1 along the alignment angle contiguous, and taking the area of ones as the intermediate area.

Alternatively, the fluence map could be segmented into one or more multileaf collimator settings.

In a determine value of intermediate cost function step 56, the treatment planning system determines a value of the intermediate exposure cost function based on the any intermediate area. For instance, the intermediate exposure cost can be an aggregation of several intermediate areas.

Using the presented method, not only are the target volumes taken into account, but this information is combined with possible segment shapes determined in a number of ways (e.g., by conforming the multileaf collimator to the target volume projections or by segmenting an optimized fluence map), and moreover with possible dose distributions (e.g., resulting from the conformed multileaf collimator, or from the optimized fluence maps, or from optimized segments resulting after segmenting the fluence maps) and the values of the objective functions evaluated on these dose distributions.

Figure 8:
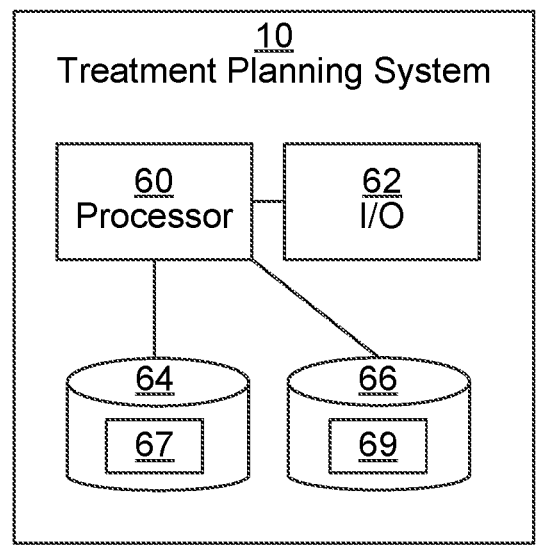
FIG. 8 is a schematic diagram illustrating components of the treatment planning system of FIG. 1 according to one embodiment.

FIG. 8 is a schematic diagram illustrating components of the treatment planning system 1 of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIGS. 7A-B above.

The memory 64 can be any combination of random access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. contain values 69 of cost functions.

The treatment planning system 1 further comprises an I/O interface 62 for communicating with other external entities. The I/O interface 62 also includes a user interface.

Other components of the treatment planning system 1 are omitted in order not to obscure the concepts presented herein.

Figure 9:
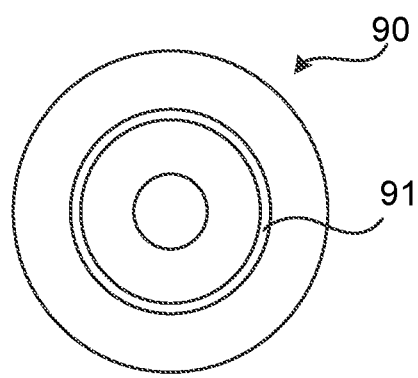
FIG. 9 shows one example of a computer program product comprising computer readable means.

FIG. 9 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 8. While the computer program 91 is here schematically shown as a track on the depicted optical disk, the computer program can be stored in any way which is suitable for the computer program product, such as a removable solid state memory, e.g. a Universal Serial Bus (USB) drive.

Here now follows a list of embodiments from another perspective, enumerated with roman numerals.

i. A method for determining arc costs of respective potential arcs of a treatment plan for use in radiation therapy targeting at least one target volume, the method being performed in a treatment planning system and comprising the steps of:
   determining a plurality of beam orientations, wherein each beam orientation comprises respective values of a couch angle, a collimator angle and a gantry angle;
   evaluating, for each beam orientation, a set of at least one cost function, wherein the at least one cost function comprises an intermediate exposure cost function that is evaluated by performing the substeps of:
   projecting the at least one target volumes on a beam plane being a normal plane to a beam direction of the beam orientation;
   determining an alignment angle based on the collimator angle value;
   finding any intermediate area in the beam plane along the alignment angle between areas of the at least one target volume projection, such that there is at most one intermediate area crossed by each line parallel to the alignment angle;
   determining a value of the intermediate exposure cost function based on the any intermediate area;
   the method further comprising the steps of:
   finding a plurality of arcs, wherein each arc comprises a sequence of a plurality of beam orientations; and
   calculating, for each arc in the plurality of arcs, at least one arc cost based on the cost function values of the beam orientations of the arc.

ii. The method according to embodiment i, wherein the step of finding any intermediate area comprises finding any intermediate area between different target volume projections.

iii. The method according to embodiment i or ii, further comprising the step of:

selecting at least one arc for use in the treatment plan based on the respective arc costs.

iv. The method according to any one of the preceding embodiments, wherein the step of finding an intermediate area comprises finding, for each of a plurality of parallel strips along the alignment angle, a strip area between areas of the at least one target volume projection, wherein each strip is associated with a pair of leafs of a multileaf collimator.

v. The method according to embodiment iv, wherein the step of finding an intermediate area comprises performing a fluence map optimization for the beam orientation and segmenting the optimized fluence map into one or more multileaf collimator settings.

vi. The method according to any one of the preceding embodiments, further comprising:
projecting at least one organ at risk on the beam plane; and
subtracting any overlap area, where an organ at risk projection and a target volume projection overlap, from the overlapped target volume projection.

vii. The method according to any one of the preceding embodiments, further comprising the step of:
projecting at least one organ at risk on the beam plane; and
wherein in the step of evaluating a set of at least one cost function, the set of at least one cost function comprises a function which penalizes any overlap area, where an organ at risk projection and the intermediate area overlap.

viii. The method according to any one of the preceding embodiments, wherein in the step of evaluating a set of at least one cost function, the set of at least one cost function comprises an intermediate dose function which quantifies an estimate of a dose to the at least one target volume.

ix. The method according to any one of the preceding embodiments, wherein in the step of evaluating a set of at least one cost function, the set of at least one cost function comprises at least one constituent function of a treatment plan optimization.

x. The method according to any one of the preceding embodiments, wherein in the step of evaluating a set of at least one cost functions, the set of at least one cost function comprises at least one function penalizing the intermediate area size from each beam orientation compared to the minimum intermediate area size over all beam orientations.

xi. The method according to any one of the preceding embodiments, wherein the step of calculating at least one arc cost comprises calculating, for each arc in the plurality arcs, an aggregate arc cost based on the cost function values of the beam orientations of the arc.

xii. The method according to any one of the preceding embodiments, wherein the step of calculating at least one arc cost, comprises calculating, for each arc in the plurality of arcs, an aggregate arc cost based on an estimate of a dose provided by the combined exposure of the beam orientations of the arc.

xiii. A treatment planning system for determining arc costs of respective potential arcs of a treatment plan for use in radiation therapy targeting at least one target volume, the treatment planning system comprising:
a processor; and
a memory storing instructions that, when executed by the processor, cause the treatment planning system to:
determine a plurality of beam orientations, wherein each beam orientation comprises respective values of a couch angle, a collimator angle and a gantry angle;
evaluate, for each beam orientation, a set of at least one cost function, wherein the at least one cost function comprises an intermediate exposure cost function that is evaluated by executing instructions that cause the treatment planning system to:
project the at least one target volumes on a beam plane being a normal plane to a beam direction of the orientation set;
determine an alignment angle based on the collimator angle value;
find any intermediate area in the beam plane along the alignment angle between areas of the at least one target volume projection, such that there is at most one intermediate area crossed by each line parallel to the alignment angle;
determine a value of the intermediate exposure cost function based on the any intermediate area;
wherein the memory further comprises instructions that, when executed by the processor, cause the treatment planning system to:
find a plurality of arcs, wherein each arc comprises a sequence of a plurality of beam orientations; and
calculate, for each arc in the plurality of arcs, at least one arc cost based on the cost function values of the beam orientations of the arc.

xiv. A computer program for determining arc costs of respective potential arcs of a treatment plan for use in radiation therapy targeting at least one target volume, the computer program comprising computer program code which, when run on a treatment planning system causes the treatment planning system to:
determine a plurality of beam orientations, wherein each beam orientation comprises respective values of a couch angle, a collimator angle and a gantry angle;
evaluate, for each beam orientation, a set of at least one cost function, wherein the at least one cost function comprises an intermediate exposure cost function that is evaluated by running computer program code which, when run on the treatment planning system causes the treatment planning system to:
project the at least one target volumes on a beam plane being a normal plane to a beam direction of the orientation set;
determine an alignment angle based on the collimator angle value;
find any intermediate area in the beam plane along the alignment angle between areas of the at least one target volume projection, such that there is at most one intermediate area crossed by each line parallel to the alignment angle;
determine a value of the intermediate exposure cost function based on the any intermediate area;
wherein the computer program further comprises computer program code which, when run on a treatment planning system causes the treatment planning system to:
find a plurality of arcs, wherein each arc comprises a sequence of a plurality of beam orientations; and
calculate, for each arc in the plurality of arcs, at least one arc cost based on the cost function values of the beam orientations of the arc.

xv. A computer program product comprising a computer program according to embodiment xiv and a computer readable means on which the computer program is stored.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for determining arc costs of respective potential arcs of a treatment plan for use in radiation therapy targeting at least one target volume, the method being performed in a treatment planning system and comprising the steps of:
   determining a plurality of beam orientations, wherein each beam orientation comprises respective values of a couch angle, a collimator angle and a gantry angle, each beam orientation defining a beam direction through a collimator;
   evaluating, for each beam orientation, a set of at least one cost function, wherein the at least one cost function comprises an intermediate exposure cost function that is evaluated by performing the substeps of:
      projecting the at least one target volume on a beam plane being a normal plane to the beam direction;
      determining an alignment of the collimator based on the collimator angle value;
      finding any intermediate area in the beam plane along the alignment between areas of the at least one target volume projection, such that there is at most one intermediate area crossed by each line parallel to the alignment; and
      determining a value of the intermediate exposure cost function based on the any intermediate area;
   finding a plurality of arcs, wherein each arc comprises a sequence of a plurality of beam orientations; and
   calculating, for each arc in the plurality of arcs, at least one arc cost based on the cost function values of the beam orientations of the arc.

2. The method according to claim 1, wherein the step of finding any intermediate area comprises finding any intermediate area between projections of different respective target volumes.

3. The method according to claim 1, further comprising the step of:
   selecting at least one arc for use in the treatment plan based on the respective arc costs.

4. The method according to claim 1, wherein the step of finding any intermediate area comprises finding, for each of a plurality of parallel strips along the alignment, a strip area between areas of the at least one target volume projection, wherein each strip is associated with a pair of leaves of a multileaf collimator.

5. The method according to claim 4, wherein the step of finding any intermediate area comprises performing a fluence map optimization for the beam orientation and segmenting the optimized fluence map into one or more multileaf collimator settings.

6. The method according to claim 1, further comprising:
   projecting at least one organ at risk on the beam plane; and
   subtracting any overlap area, where an organ at risk projection and a target volume projection overlap, from an overlapped target volume projection.

7. The method according to claim 1 further comprising the step of:
   projecting at least one organ at risk on the beam plane; and
   wherein in the step of evaluating a set of at least one cost function, the set of at least one cost function comprises a function which penalizes any overlap area, where an organ at risk projection and the intermediate area overlap.

8. The method according to claim 1, wherein in the step of evaluating a set of at least one cost function, the set of at least one cost function comprises an intermediate dose function which quantifies an estimate of a dose to the at least one target volume.

9. The method according to claim 1, wherein in the step of evaluating a set of at least one cost function, the set of at least one cost function comprises at least one constituent function of a treatment plan optimization.

10. The method according to claim 1, wherein in the step of evaluating a set of at least one cost function, the set of at least one cost function comprises at least one function penalizing a size of the intermediate area from each beam orientation compared to a minimum size of the intermediate area over all beam orientations.

11. The method according to claim 1, wherein the step of calculating at least one arc cost comprises calculating, for each arc in the plurality arcs, an aggregate arc cost based on the cost function values of the beam orientations of the arc.

12. The method according to claim 1, wherein the step of calculating at least one arc cost, comprises calculating, for each arc in the plurality of arcs, an aggregate arc cost based on an estimate of a dose provided by the combined exposure of the beam orientations of the arc.

13. A treatment planning system for determining arc costs of respective potential arcs of a treatment plan for use in radiation therapy targeting at least one target volume, the treatment planning system comprising:
   a processor; and
   a memory storing instructions that, when executed by the processor, cause the treatment planning system to:
      determine a plurality of beam orientations, wherein each beam orientation comprises respective values of a couch angle, a collimator angle and a gantry angle, each beam orientation defining a beam direction through a collimator;
      evaluate, for each beam orientation, a set of at least one cost function, wherein the at least one cost function comprises an intermediate exposure cost function that is evaluated by executing instructions that cause the treatment planning system to:
         project the at least one target volume on a beam plane being a normal plane to the beam direction;
         determine an alignment of the collimator based on the collimator angle value;
         find any intermediate area in the beam plane along the alignment between areas of the at least one target volume projection, such that there is at most one intermediate area crossed by each line parallel to the alignment; and
         determine a value of the intermediate exposure cost function based on the any intermediate area;
   wherein the memory further comprises instructions that, when executed by the processor, cause the treatment planning system to:
      find a plurality of arcs, wherein each arc comprises a sequence of a plurality of beam orientations; and
      calculate, for each arc in the plurality of arcs, at least one arc cost based on the cost function values of the beam orientations of the arc.

14. A computer program for determining arc costs of respective potential arcs of a treatment plan for use in radiation therapy targeting at least one target volume, the computer program comprising computer program code which, when run on a treatment planning system causes the treatment planning system to:

determine a plurality of beam orientations, wherein each beam orientation comprises respective values of a couch angle, a collimator angle and a gantry angle, each beam orientation defining a beam direction through a collimator;

evaluate, for each beam orientation, a set of at least one cost function, wherein the at least one cost function comprises an intermediate exposure cost function that is evaluated by running computer program code which, when run on the treatment planning system causes the treatment planning system to:

project the at least one target volume on a beam plane being a normal plane to the beam direction;

determine an alignment of the collimator based on the collimator angle value;

find any intermediate area in the beam plane along the alignment between areas of the at least one target volume projection, such that there is at most one intermediate area crossed by each line parallel to the alignment; and determine a value of the intermediate exposure cost function based on the any intermediate area;

wherein the computer program further comprises computer program code which, when run on the treatment planning system causes the treatment planning system to:

find a plurality of arcs, wherein each arc comprises a sequence of a plurality of beam orientations; and calculate, for each arc in the plurality of arcs, at least one arc cost based on the cost function values of the beam orientations of the arc.

15. A computer program product comprising a computer program according to claim 14 and a non-transitory computer readable medium on which the computer program is stored.

* * * * *